US012788615B2

(12) United States Patent
Farrar et al.

(10) Patent No.: US 12,788,615 B2
(45) Date of Patent: Nov. 10, 2026

(54) MICTURITION DEVICE

(71) Applicant: ConneXion Strategies LLC, Southgate, KY (US)

(72) Inventors: Lynn A. Farrar, Southgate, KY (US); Margaret S. Fradette, Narragansett, RI (US); William M. Fradette, Narragansett, RI (US); Thomas E. Kramer, Andover, MN (US); David J. Prince, St. Paul, MN (US); Ryan Barnes, Maple Lake, MN (US)

(73) Assignee: Connexion Strategies LLC, Southgate, KY (US)

( * ) Notice: Subject to any disclaimer, the term of this patent is extended or adjusted under 35 U.S.C. 154(b) by 0 days.

(21) Appl. No.: 17/482,021

(22) Filed: Sep. 22, 2021

(65) Prior Publication Data

US 2022/0087853 A1 Mar. 24, 2022

Related U.S. Application Data

(60) Provisional application No. 63/082,302, filed on Sep. 23, 2020.

(51) Int. Cl.
*A61F 5/455* (2006.01)
*A61F 5/44* (2006.01)

(52) U.S. Cl.
CPC ............ *A61F 5/455* (2013.01); *A61F 5/4404* (2013.01); *A61F 5/4556* (2013.01)

(58) Field of Classification Search
CPC ...... A61F 5/4408; A61F 5/455; A61F 5/4404; A61F 5/4556; A61B 9/005; A61B 9/04; A61B 9/12
See application file for complete search history.

(56) References Cited

U.S. PATENT DOCUMENTS

| | | | |
|---|---|---|---|
| 4,063,548 A | 12/1977 | Klatt et al. | |
| 4,202,057 A | 5/1980 | Ibarra | |
| 4,258,032 A | 3/1981 | Mehl | |
| 4,270,539 A * | 6/1981 | Frosch | A61F 5/455 604/347 |
| 4,336,880 A | 6/1982 | Mehl | |
| 4,343,316 A | 8/1982 | Jespersen | |
| 4,422,188 A | 12/1983 | Strutton et al. | |

(Continued)

FOREIGN PATENT DOCUMENTS

WO 2019212954 A1 11/2019

*Primary Examiner* — Philip R Wiest
*Assistant Examiner* — Peter Daniel Smith

(57) ABSTRACT

A micturition device for fluid removal. The micturition device includes a micturition cup configured to encircle a user's urethra and vaginal anatomy and to facilitate evacuating a fluid from the micturition cup. The micturition cup is joined to a slide plate to form a common flow passage from the micturition cup through the slide plate. A garment, configured to be worn over a pelvic area, includes a slide track. The slide plate slidably engages with the slide track to allow a user to adjust a position of the micturition device relative to the user's vaginal anatomy in a seated or laying position and/or on the positioning of a seat. Also, a method of using the micturition device. Further, a micturition system for evacuating and receiving a fluid from the micturition device.

13 Claims, 7 Drawing Sheets

(56) References Cited

U.S. PATENT DOCUMENTS

| | | | | | |
|---|---|---|---|---|---|
| 4,615,692 | A * | 10/1986 | Giacalone | A61F 5/455 604/179 |
| 4,631,061 | A * | 12/1986 | Martin | A61F 5/451 604/323 |
| 4,804,377 | A | 2/1989 | Hanifl et al. | |
| 4,846,817 | A * | 7/1989 | Mohr | A61F 5/455 604/329 |
| 4,889,532 | A * | 12/1989 | Metz | A61F 5/44 4/144.3 |
| 4,889,533 | A * | 12/1989 | Beecher | A61F 5/4407 604/355 |
| 5,002,541 | A | 3/1991 | Conkling et al. | |
| 5,053,027 | A * | 10/1991 | Manfredi | A61F 5/455 604/327 |
| 5,082,006 | A | 1/1992 | Jonasson | |
| 5,358,148 | A | 10/1994 | Hanifl et al. | |
| 5,411,495 | A | 5/1995 | Willingham | |
| 5,876,395 | A | 3/1999 | Hart et al. | |
| 5,891,051 | A | 4/1999 | Han et al. | |
| 5,894,608 | A | 4/1999 | Birbara | |
| 6,183,454 | B1 * | 2/2001 | Levine | A61F 5/4556 604/355 |
| 6,311,339 | B1 | 11/2001 | Kraus | |
| 6,342,049 | B1 | 1/2002 | Nichols | |
| 6,398,742 | B1 | 6/2002 | Kim | |
| 6,409,971 | B1 | 6/2002 | Wilkinson et al. | |
| 6,592,560 | B2 | 7/2003 | Snyder | |
| 6,702,793 | B1 | 3/2004 | Sweetser | |
| 6,716,200 | B2 | 4/2004 | Bracken et al. | |
| 6,732,384 | B2 | 5/2004 | Scott | |
| 6,740,066 | B2 | 5/2004 | Wolff et al. | |
| 6,857,137 | B2 | 2/2005 | Otto | |
| 6,904,621 | B2 | 6/2005 | Otto et al. | |
| 6,931,276 | B2 | 8/2005 | Streng et al. | |
| 7,160,276 | B2 | 1/2007 | Bruns | |
| 7,585,293 | B2 | 9/2009 | Vermaak | |
| 7,931,630 | B2 | 4/2011 | Nishtala et al. | |
| 7,993,322 | B2 | 8/2011 | Brud et al. | |
| 8,043,230 | B2 | 10/2011 | Deadwyler et al. | |
| 8,303,554 | B2 | 11/2012 | Tsai et al. | |
| 8,597,207 | B1 | 12/2013 | Perry | |
| 8,672,916 | B2 | 3/2014 | Brud et al. | |
| 9,216,242 | B2 | 12/2015 | Nishtala et al. | |
| 9,233,020 | B2 | 1/2016 | Matsumiya | |
| 10,226,376 | B2 | 3/2019 | Sanchez et al. | |
| 10,376,406 | B2 | 8/2019 | Newton | |
| 10,376,407 | B2 | 8/2019 | Newton | |
| 10,390,989 | B2 | 8/2019 | Sanchez et al. | |
| 10,568,756 | B1 | 2/2020 | Heckerman | |
| 10,588,774 | B2 | 3/2020 | Alhaqqan | |
| 10,716,699 | B2 | 7/2020 | Parr et al. | |
| 10,806,623 | B2 * | 10/2020 | VanMiddendorp | A61F 5/441 |
| 10,850,014 | B2 | 12/2020 | Newton | |
| 10,857,025 | B2 | 12/2020 | Davis et al. | |
| 10,952,889 | B2 | 3/2021 | Newton et al. | |
| 10,973,678 | B2 | 4/2021 | Newton et al. | |
| 11,000,401 | B2 | 5/2021 | Ecklund et al. | |
| 2002/0193760 | A1 | 12/2002 | Thompson | |
| 2004/0082926 | A1 | 4/2004 | Bruns | |
| 2006/0005307 | A1 | 1/2006 | Arguelles | |
| 2007/0010797 | A1 | 1/2007 | Nishtala et al. | |
| 2010/0137743 | A1 | 6/2010 | Nishtala et al. | |
| 2010/0331798 | A1 | 12/2010 | Block | |
| 2011/0178425 | A1 | 7/2011 | Nishtala et al. | |
| 2011/0251572 | A1 | 10/2011 | Nishtala et al. | |
| 2016/0051176 | A1 | 2/2016 | Ramos et al. | |
| 2016/0374848 | A1 | 12/2016 | Sanchez et al. | |
| 2017/0266031 | A1 | 9/2017 | Sanchez et al. | |
| 2017/0281399 | A1 | 10/2017 | VanMiddendorp et al. | |
| 2017/0312405 | A1 | 11/2017 | Newton | |
| 2017/0348139 | A1 | 12/2017 | Newton et al. | |
| 2018/0028348 | A1 | 2/2018 | Newton | |
| 2018/0028349 | A1 | 2/2018 | Newton et al. | |
| 2018/0049910 | A1 | 2/2018 | Newton | |
| 2018/0168853 | A1 | 6/2018 | Newton | |
| 2018/0228642 | A1 | 8/2018 | Davis et al. | |
| 2018/0304045 | A1 | 10/2018 | Glithero et al. | |
| 2019/0142624 | A1 | 5/2019 | Sanchez et al. | |
| 2019/0224036 | A1 | 7/2019 | Sanchez et al. | |
| 2019/0240063 | A1 | 8/2019 | Doreswamy et al. | |
| 2019/0247222 | A1 | 8/2019 | Ecklund et al. | |
| 2019/0282391 | A1 | 9/2019 | Johannes et al. | |
| 2019/0307597 | A1 | 10/2019 | Newton | |
| 2019/0307598 | A1 | 10/2019 | Newton | |
| 2019/0314190 | A1 | 10/2019 | Sanchez et al. | |
| 2019/0350565 | A1 | 11/2019 | Hiddleson | |
| 2019/0358075 | A1 | 11/2019 | Scharich, III et al. | |
| 2019/0365561 | A1 | 12/2019 | Newton et al. | |
| 2020/0046544 | A1 * | 2/2020 | Godinez | A61F 5/451 |
| 2020/0121491 | A1 | 4/2020 | Berry | |
| 2020/0306075 | A1 | 10/2020 | Newton et al. | |
| 2020/0315836 | A1 | 10/2020 | Radl et al. | |
| 2020/0315837 | A1 | 10/2020 | Radl et al. | |
| 2020/0315838 | A1 | 10/2020 | Eckert | |
| 2020/0375781 | A1 | 12/2020 | Staali et al. | |
| 2020/0390591 | A1 * | 12/2020 | Glithero | A61F 5/455 |
| 2021/0000637 | A1 | 1/2021 | VanMiddendorp et al. | |
| 2021/0023279 | A1 | 1/2021 | Radl et al. | |
| 2021/0059853 | A1 | 3/2021 | Davis et al. | |
| 2021/0069005 | A1 | 3/2021 | Sanchez et al. | |
| 2021/0069006 | A1 | 3/2021 | Waitkus et al. | |
| 2021/0069008 | A1 | 3/2021 | Blabas et al. | |
| 2021/0113749 | A1 | 4/2021 | Radl et al. | |
| 2021/0137724 | A1 | 5/2021 | Ecklund et al. | |
| 2021/0170079 | A1 | 6/2021 | Radl et al. | |
| 2021/0177644 | A1 | 6/2021 | Heckerman | |
| 2021/0186744 | A1 | 6/2021 | Spector | |

* cited by examiner

MICTURITION DEVICE

CROSS-REFERENCE TO RELATED APPLICATIONS

This application is related to and claims priority to U.S. Provisional Patent Application Ser. No. 63/082,302, filed on Sep. 23, 2020 (pending), the entire content of which is herein incorporated by reference in its entirety.

TECHNICAL FIELD

This application relates generally to bodily fluid removal during an aircraft flight. More specifically, this application describes a device, system, and method of use thereof to aid a female pilot in voiding bodily fluid in a confined condition, such as in-flight.

BACKGROUND OF THE INVENTION

Nature can call at inopportune moments. For example, nature can call mid-flight for a pilot. A pilot, particularly, a female pilot, confronted with the need to void her bladder mid-flight faces a difficult decision. Does she void her bladder into a diaper that pilots often wear during long flights? In doing so, she will endure an uncomfortable rest of her flight as well as risk tissue maceration from prolonged exposure to moisture. Or does she try to hold it and risk a urinary tract infection? Neither choice is appealing. Moreover, the inconvenience and messiness of voiding mid-flight can cause some pilots to dehydrate with accompanying negative impacts on energy, cognition, and judgement. Thus, it would be desirable to provide a female pilot with a more desirable alternative option for voiding her bladder mid-flight. Specifically, it would be desirable to provide an alternative device, system, and/or method that avoids or minimizes known issues with existing mid-flight bladder voiding options.

SUMMARY OF THE INVENTION

In accordance with embodiments of the invention, aspects of a micturition device, system, and a corresponding method for use thereof are described. Aspects of a micturition device, system, and a corresponding method for use thereof help to avoid the problems associated with existing devices, systems, and methods. Specifically, the aspects of a micturition device described herein provide for systems and methods to void bodily fluid in flight.

In one implementation of the invention, a micturition device for fluid removal is disclosed. The micturition device includes a micturition cup. The micturition cup is configured to encircle vaginal area anatomy (urethra and vagina). The micturition cup includes a rim gasket atop a semi-flexible sidewall. The semi-flexible sidewall extends outwards from a semi-rigid cup floor. The semi-rigid cup floor features an outlet port for evacuating fluid from the micturition cup. The micturition device further includes a slide plate. The slide plate includes a fitting. The fitting is configured to connect, at an end, to the outlet port to join the micturition cup and the slide plate together and to form a common flow passage from the micturition cup through the slide plate.

In one embodiment, the micturition device further includes a garment. The garment is configured to be worn over a pelvic area. The garment includes a slide track and the fitting, at an opposite end, is configured to slidably engage with the slide track. The opposite end of the fitting includes a pair of channels. The channels are configured to engage with the slide track. The slide track is configured to slide within the channels to adjust a position of the micturition device relative to the vaginal anatomy. The garment may be a compression short (or panties). The compression short is configured to hold the micturition cup securely in place. The slide track can be made of plastic.

In another embodiment, the vaginal anatomy includes a urethral opening. The vaginal anatomy may further include a vaginal opening. The rim gasket is configured to mold to the vaginal anatomy and create a seal around the vaginal anatomy. The rim gasket is formed from an elastomeric material.

In yet another embodiment, the opposite end of the fitting includes an orifice. The orifice is configured to connect to a disposable tube to join the micturition cup to the disposable tube by the slide plate and to form the common flow passage from the micturition cup to the disposable tube for further evacuation of fluid from the micturition cup.

In a further embodiment, the micturition cup and the slide plate are integrally formed with each other. In such an embodiment, the fitting is separate from the slide plate and micturition cup.

In another implementation of the invention, a method of using a micturition device is disclosed. The method includes providing a micturition device. The micturition device includes a micturition cup. The micturition cup is configured to encircle vaginal area anatomy. The micturition cup includes an outlet port for evacuating fluid from the micturition cup. The micturition device further includes a slide plate. The slide plate includes a fitting configured to connect to the outlet port to form a common flow passage from the micturition cup through the slide plate. The micturition device further includes a garment. The garment is configured to be worn over a pelvic area. The garment includes a slide track. The fitting is configured to slidably engage with the slide track. The method further includes attaching the micturition cup to the slide plate by connecting the outlet port to the fitting and forming the common flow passage from the micturition cup through the slide plate. The method further includes attaching the slide plate to the garment by engaging the fitting with the slide track and thereby removably fixing the slide plate to the garment.

In one embodiment, the method further includes adjusting a position of the micturition cup relative to the garment. The method further includes sliding the slide plate along the slide track of the garment.

In another embodiment, the method further includes attaching a disposable tube to the fitting to form the common flow passage from the micturition cup to the disposable tube for further evacuation of fluid from the micturition cup. The disposable tube may include a connector to interface with the fitting of the slide plate.

In a further implementation of the invention, a micturition system for fluid removal is disclosed. The micturition system includes a micturition device. The micturition device includes a micturition cup. The micturition cup is configured to encircle vaginal area anatomy. The micturition cup includes an outlet port for evacuating fluid from the micturition cup. The micturition device further includes a slide plate. The slide plate includes a fitting configured to connect to the outlet port to form a common flow passage from the micturition cup through the slide plate. The micturition device further includes a garment. The garment is configured to be worn over a pelvic area. The garment includes a slide track. The fitting is configured to slidably engage with the slide track. The micturition system further includes a disposable tube. The disposable tube is configured to connect to the fitting to transport fluid away from the micturition cup. The micturition system further includes a vacuum tube. The vacuum tube is configured to connect to the disposable tube to transport fluid away from the disposable tube. The micturition system further includes a receptacle. The receptacle is configured to connect to the vacuum tube and to receive fluid from the vacuum tube. The micturition system further includes a vacuum source. The vacuum source is configured to connect to the vacuum tube and to create a negative pressure to draw a fluid away from the micturition cup. The micturition system further includes a pressure controller. The pressure controller is configured to adjust the negative pressure.

In one embodiment, the micturition system further includes a bag configured to transport and store the receptacle and the vacuum source. The pressure controller may have at least a low pressure setting and a high pressure setting.

The steps and elements described herein as part of various embodiments and aspects can be reconfigured and combined in different combinations to achieve the technical effects as may be desired. To this end, the embodiments and aspects can be combined in any combination or sub-combination.

BRIEF DESCRIPTION OF THE DRAWINGS

Various additional features and advantages of the invention will become more apparent to those of ordinary skill in the art upon review of the following detailed description of one or more illustrative embodiments taken in conjunction with the accompanying drawings. The accompanying drawings, which are incorporated in and constitute a part of this specification, illustrate one or more embodiments of the invention and, together with the general description given above and the detailed description given below, serve to explain the one or more embodiments of the invention.

DETAILED DESCRIPTION OF THE INVENTION

Figure 1:
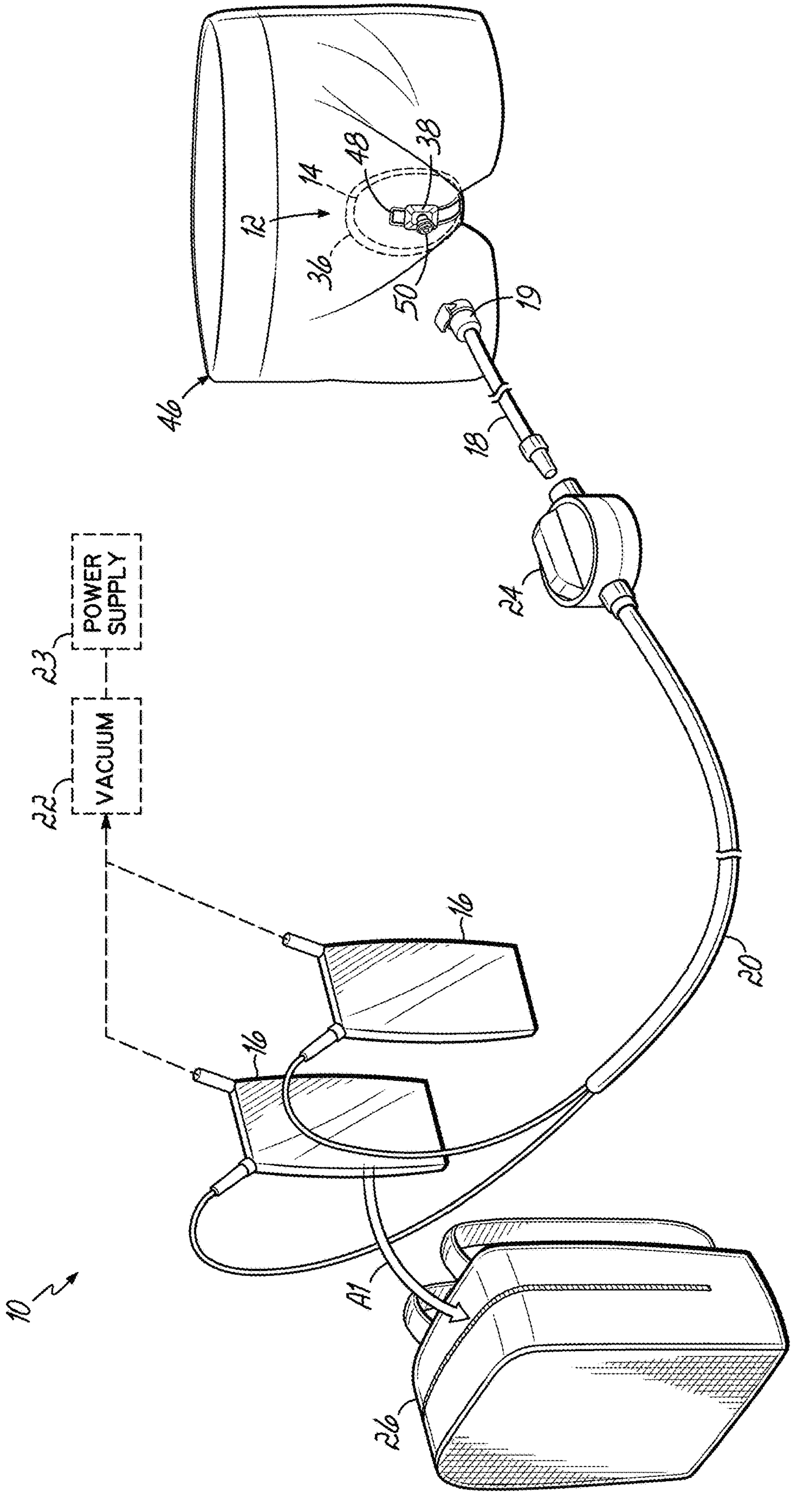
FIG. 1 is a perspective view of a micturition system.

FIG. 1 shows an exemplary embodiment of a micturition system 10. The system 10 described herein provides for voiding a bodily fluid (e.g., urine, menstrual flow), such as, for example mid-flight using negative pressure. Although the examples discussed herein use in-flight applications as examples, the present invention goes beyond such applications and can be used in other scenarios. The system 10 is configured to be prepared pre-flight, for example. It is not necessary to change any part of the system 10 during flight. Contortions by a pilot mid-flight are thus minimized. The system 10 provides for optimal, hydrated flight performance by minimizing voiding as a distracting mid-mission effort. As such, a pilot does not need to avoid in-flight hydration and a pilot does not need to "hold it" and risk infection.

As set forth in greater detail below, the system 10 includes a micturition device 12 connected to one or more receptacles 16 for receiving fluid from the micturition cup 14. A series of tubes (e.g., disposable tube 18 and vacuum tube 20) connect the micturition cup 14 to the receptacle 16. The disposable tube 18 connects to the device 12 via a connector 19 (e.g., snap fit). The vacuum tube 20 may be a multi-lumen tube wherein the number of lumens corresponds to the number of receptacles 16. The receptacle may be one or more 2000 mL collection bags with high burst strength. Smaller collection bags (e.g., 500 mL or 1000 mL) could be substituted. The receptacles 16, in one embodiment, are disposable. The receptacles 16 may include a material (e.g., moisture absorbent granules) within the receptacle 16 that causes fluids to solidify, semi-solidify, or gel once they contact the material. The addition of such a material would help to reduce mess or minimize the chance for aircraft instrumentation shortage that could be caused by accidental breakage of the receptacles 16.

With continued reference to FIG. 1, a vacuum source 22 acts through the hoses and draws the fluid from the micturition cup 14, through the disposable tube 18 and vacuum tube 20, and into the receptacles 16. Various different vacuum sources and receptacle arrangements may be used to bring vacuum pressure to the system. The vacuum source 22 may reside within the receptacles 16. For example, the vacuum source 22 and receptacle may be implemented in a unitary housing and may be kinetically-powered (e.g., spring loaded and free of pumps) and function to create negative pressure when a receptacle 16 is expanded from a compacted state (e.g., filled with air). For example, a kinetically powered, spring-loaded plastic vacuum pack may be used, such as has been used in wound care and would eliminate the need for mechanical or electro-mechanical systems requiring power. Alternatively, the vacuum source 22 may reside exterior to the receptacles 16 and include a mechanical or electro-mechanical vacuum powered by a power source 23 (e.g., batteries, etc.). The vacuum source 22 in various of the noted embodiments is controlled by the pressure controller 24.

Both the disposable tube 18 and the vacuum tube 20 connect to the pressure controller 24. The disposable tube 18 connects to the pressure controller 24 by a snap-lock sealed valve on a distal end (e.g., away from the device 12) of the disposable tube 18. The pressure controller 24 may be a dial controller and have a number of settings. For example, the pressure controller 24 can have two settings-on and off. Alternatively, the pressure controller 24 can have three settings-off, on (low), and on (high). "Low" and "high" are understood to mean relative amounts of negative pressure generated by the vacuum source 22 for drawing fluid through the tubes 18, 20. The pressure controller 24 may be set to "high" when a user is purposefully emptying her bladder, for example. The pressure controller 24 may be set to "low" to remove small amounts of excess moisture (e.g., between voidings). Removing excess moisture on the "low" setting helps to keep the vaginal area dry and helps to minimize possible tissue maceration from caustic urine over long flights. Such a setting would also be helpful for managing the unpredictability of menstrual flow. Still further, the low setting may also provide reinforcement for the rim gasket or seal 32 to be used on the cup rim to add further protection against leakage. The pressure controller 24 may be secured, by Velcro or similar, to a strap on user's thigh. Alternative locations for the pressure controller 24 are contemplated. The pressure controller 24 strapped to a user's thigh allows for one-handed control of micturition while in flight, for example.

With continued reference to FIG. 1, for ease of transport or storage, the one or more receptacles 16 and for vacuum source(s) 22 (and power source 23, if applicable) can be stored in a bag 26, as illustrated by arrow A1. The bag 26 could be a backpack or similar configured to receive the receptacle 16 and vacuum source 22 (and power source 23, if applicable). In a cockpit, the bag 26 could be located behind a pilot's seat and secured to the floor with a Velcro plate, or similar. Alternatively, a smaller receptacle 16 and a smaller vacuum source 22 could be located in a pocket of a user's clothing—for example, in a pants pocket of a flight suit. Because the cup 14, disposable tube 18, pressure controller 24, vacuum tube 20, and receptacles 16 are all disposable, no special cleaning of the system 10 is required.

The features of the system 10 are set forth in further detail below to clarify each of the functional advantages and other benefits provided in this disclosure. Other advantages and technical effects of the embodiments of this invention will become evident to one skilled in the art from the following description.

Figure 2B:
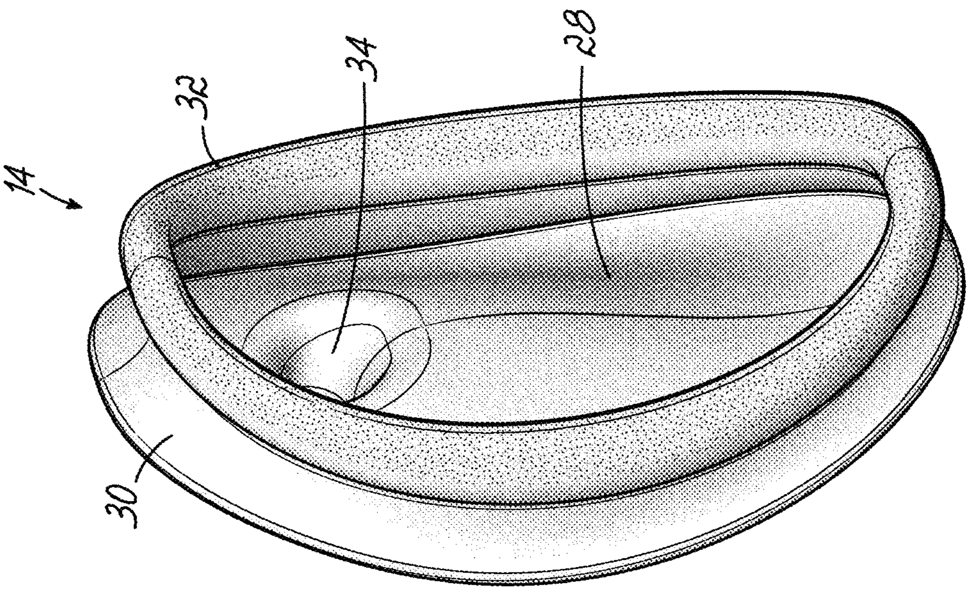
FIG. 2B is an alternative perspective view of the micturition cup.
Figure 2A:
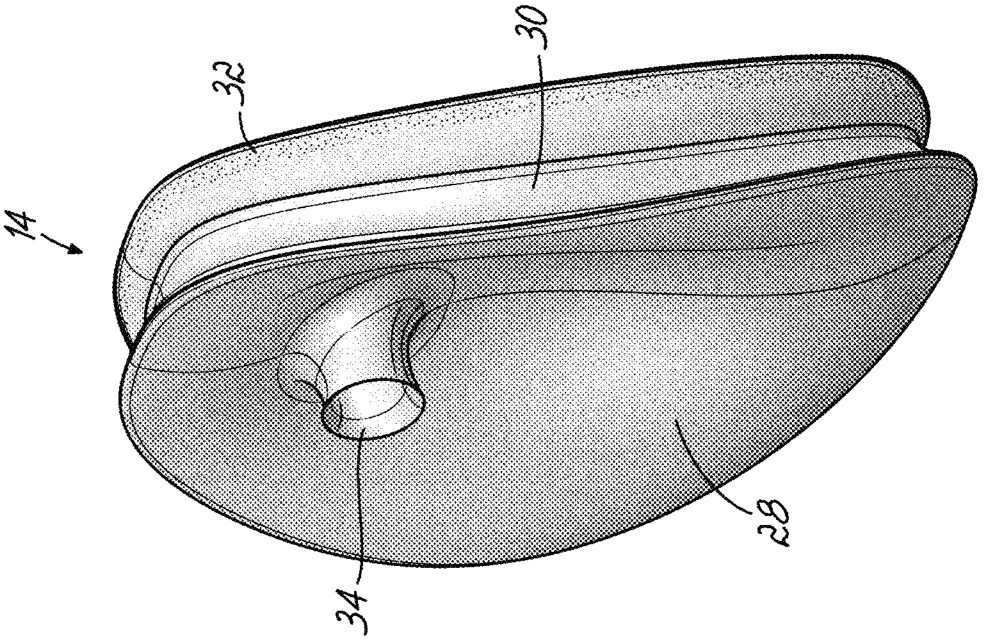
FIG. 2A is a perspective view of a micturition cup.

FIGS. 2A and 2B show perspectives of an exemplary embodiment of a micturition cup or interface 14. The cup 14 may come in different sizes to accommodate variations in vaginal-area anatomy. Further, the cup 14 may be disposable (e.g., one-flight-use) and made of thermoplastic. The cup 14 includes a cup floor 28. The cup floor 28 can be made of a semi-rigid material such as a plastic, for example. Extending outward from the cup floor 28 is a flexible sidewall 30. The sidewall 30 can be made of a semi-flexible material such as a plastic, for example. The plastic of the sidewall 30 may be more flexible than the plastic of the cup floor 28. Atop the rim of the sidewall 30 is a rim gasket or seal 32. The rim gasket or seal 32 can be made of an elastomeric material that molds to and can be comfortably situated against a user's skin to create a comfortable seal. For example, the rim gasket 32 could be made of a biocompatible hydrogel or other similar material (e.g., silicone). The rim gasket 32 in one embodiment is intended to be located within the labial wall area (e.g., held by the labial folds) to provide a secure fit for the cup 14.

The micturition cup 14 includes an outlet port 34. In the depicted embodiment, the outlet port 34 is located on the cup floor 28. The outlet port 34 provides a path for a fluid (e.g., urine, menstrual flow) in the micturition cup 14 to exit the cup 14. The cup floor 28 is contoured to direct the flow of a fluid in the cup 14 towards the outlet port 34 to encourage the fluid to leave the cup 14. In one embodiment of the invention, an interior of the cup 14 may be coated with a coating. The coating may be a hydrophobic coating material to prevent a fluid (e.g., urine) from sticking to the cup 14 and to further encourage fluid to flow to the outlet port 34. Alternatively, the coating could be an anti-coagulant coating material to prevent a fluid (e.g., menstrual flow) from sticking to or accumulating within the cup 14. For example, a heparin coating may be used. Alternative coating materials are also contemplated.

The micturition cup 14, as depicted in FIGS. 2A and 2B, is ergonomically contoured to encircle the vaginal area anatomy of a user (e.g., a female pilot). "Vaginal area anatomy", as used herein, is understood to encompass the external vaginal area including the urethral opening. As such, the embodiment of the cup 14 of FIGS. 2A and 2B will cover both the urethral opening and vaginal opening of a wearer. This allows for the cup 14 to collect both urine and menstrual flow from a female wearer-reducing leaks and avoiding the use of diapers or pads. In an alternative embodiment, the cup 14 may be sized such that the cup 14 covers the urethral opening, but not the vaginal opening. In such an alternative embodiment, the cup 14 would be capable of collecting urine, but not as capable of collecting menstrual flow. The relative dimensions of a cup 14 configured to cover both the urethral opening and vaginal opening of a wearer could be made different than the dimensions of a cup 14 configured to cover the urethral opening, but not the vaginal opening. Such is shown, for example, in FIG. 8. The length, width, and height of the cup 14 may vary depending on the intended use of the cup 14 (e.g., covering both the urethra opening and vaginal opening or covering the urethra opening, but not the vaginal opening). Furthermore, depending on the anatomy of a wearer, the cap 14 may be sized accordingly for different users. That is, for example, there may be longer or smaller user sizes.

Figure 3:
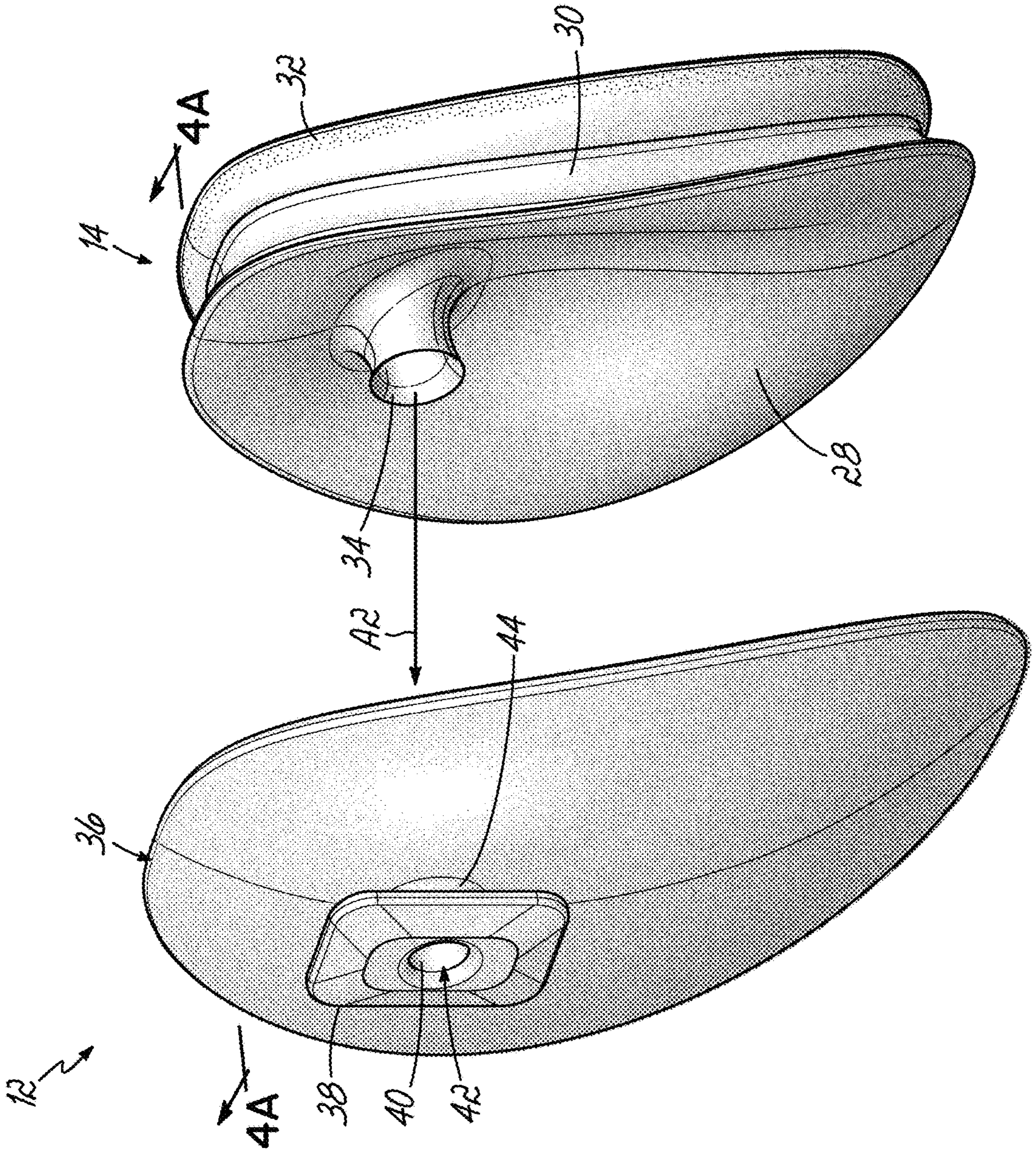
FIG. 3 is a perspective view of a micturition device.

FIG. 3 shows an exemplary embodiment of a micturition device 12. The micturition device 12 includes a micturition cup 14, as described above with respect FIGS. 2A and 2B, and a slide plate 36. The slide plate 36 is shaped complementary to the cup 14-particularly, to the cup floor 28. The slide plate 36 includes a low-profile slide fitting 38. The slide fitting 38 extends through the slide plate 36 such that one end of the fitting 38 is located on one side of the slide plate 36 (e.g., the side of the slide plate 36 that faces the cup 14) and the opposite end of the fitting 38 is located on an opposing side of the slide plate 36 (e.g., the side of the slide plate that faces away from the cup 14).

Each end of the slide fitting 38 includes an orifice 40. The orifices 40 are connected by a passage 42. The passage 42 is configured to allow a fluid (e.g., urine, menstrual flow) to flow through the passage 42. The fitting 38 also includes channels 44 between an opposite end of the fitting 38 and a surface of the slide plate 36. The channels 44 are configured to interact with another aspect of the micturition system 10, as described in greater detail below. As illustrated by arrow A2, the cup 14 and the slide plate 36 are configured to engage with one another, as described in greater detail below with respect to FIGS. 4A and 4B.

Figure 4B:
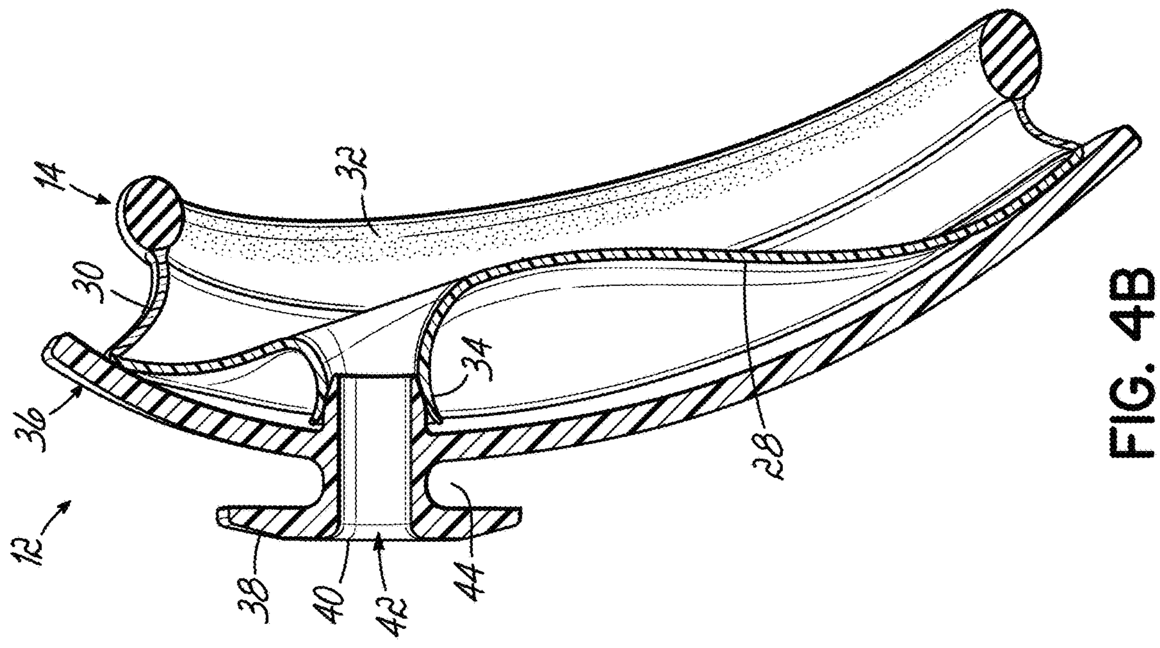
FIG. 4B is an alternative cross-sectional view of the micturition device.
Figure 4A:
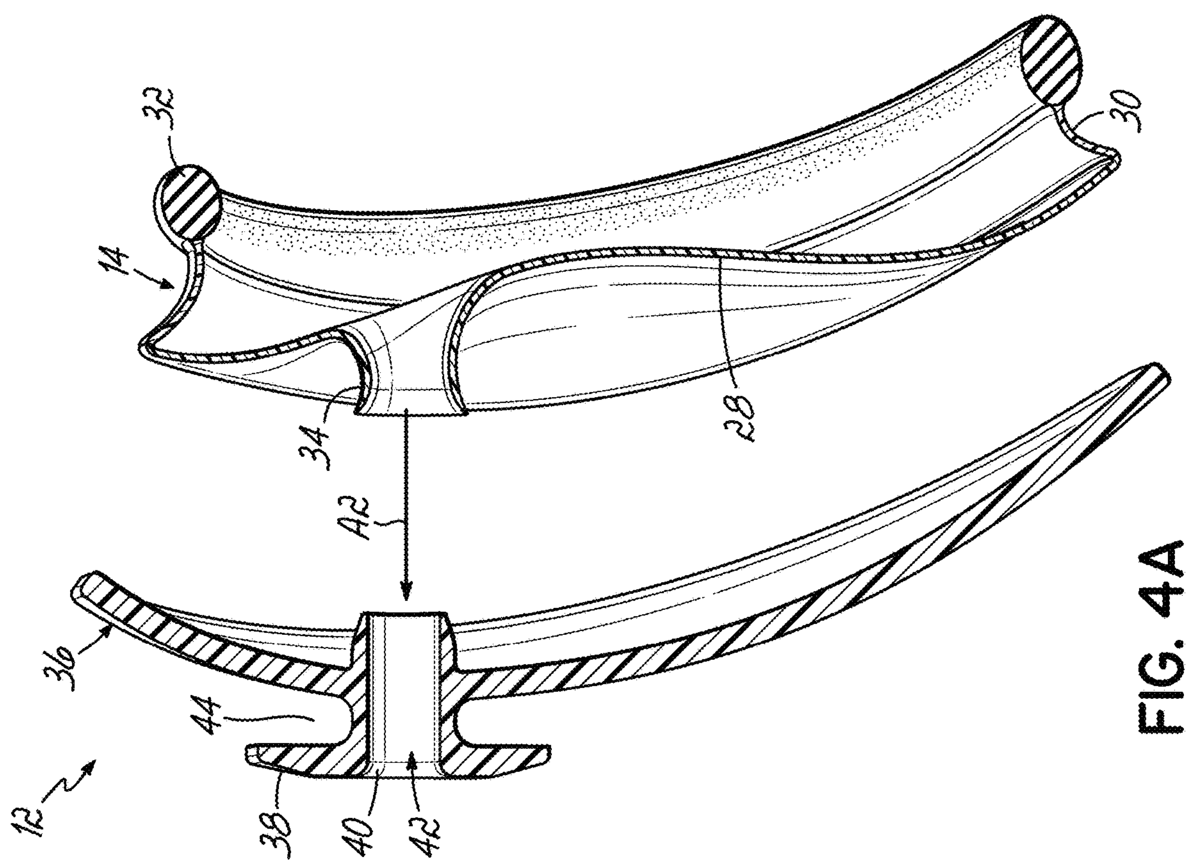
FIG. 4A is a cross-sectional view of the micturition device taken along line 4A-4A in FIG. 3.

In one embodiment, the slide plate is a separate piece from the cup. It is then joined in use of the system. For example, FIGS. 4A and 4B show cross-sections of the micturition device 12. Particularly, FIG. 4A shows the cup 14 and the slide plate 36 separated from each other. In contrast, FIG. 4B shows the cup 14 and the slide plate 36 joined to each other. As shown, the outlet port 34 of the cup 14 engages (e.g., by snap fitting) with the end of the fitting 38 to form a continuous flow path from the cup 14, through the outlet port 34, and through the passage 42 and orifice 40 and then to connect with another aspect of the micturition system 10, as described in greater detail below.

Figure 7:
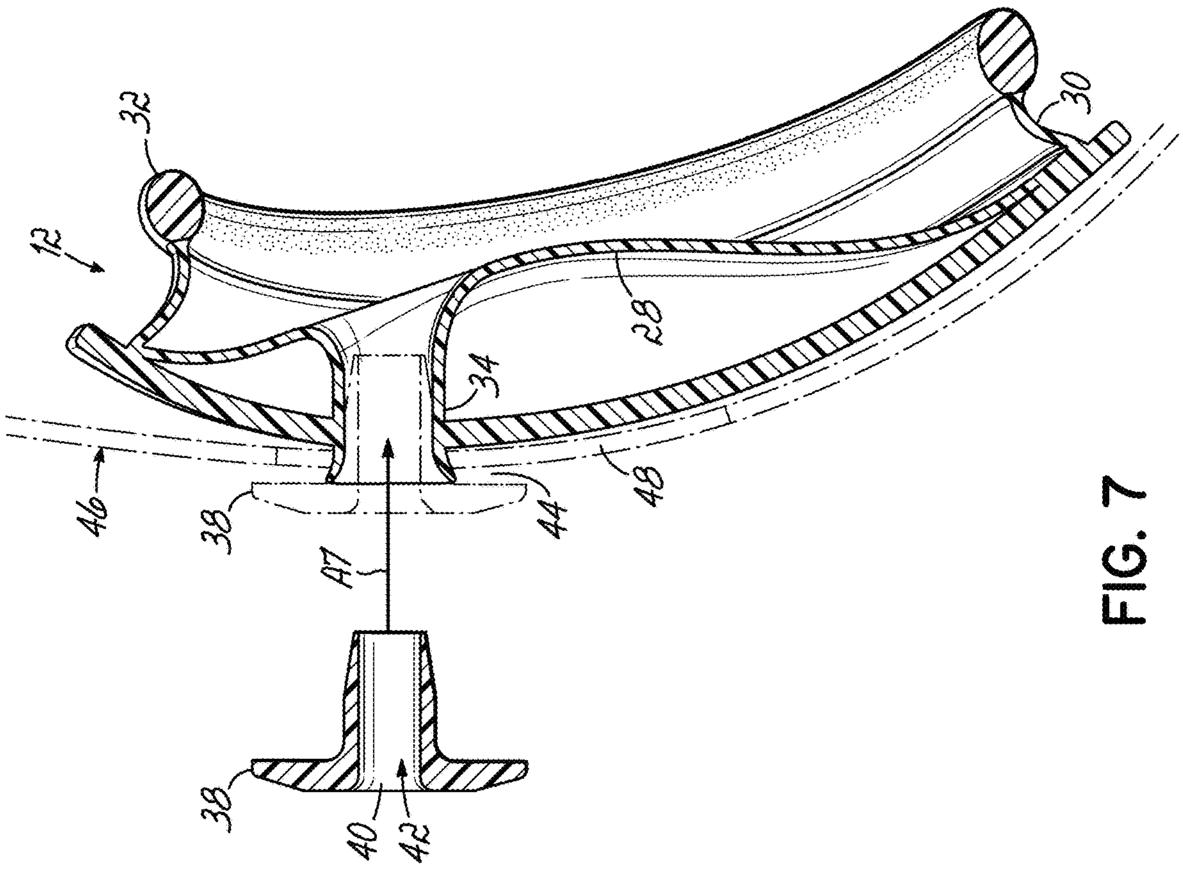
FIG. 7 is a cross-sectional view of an alternative embodiment of the micturition device.

In an alternative embodiment, as shown best in FIG. 7, the cup 14 and the slide plate 36 may be of a unitary construction. In other words, the cup 14 and slide plate 36 may be integrally formed with one another. As such, in the alternative embodiment it would not be necessary to join the cup 14 and the slide plate 36 together for use. For example, the cup 14 and slide plate 36 (e.g., micturition device 12) shown in FIG. 4B could be configured, as is the case in FIG. 7, such that the cup 14 and slide plate 36 are not separable from each other. The alternative embodiment of the device 12 is described in greater detail below with respect to FIG. 7.

Figure 5:
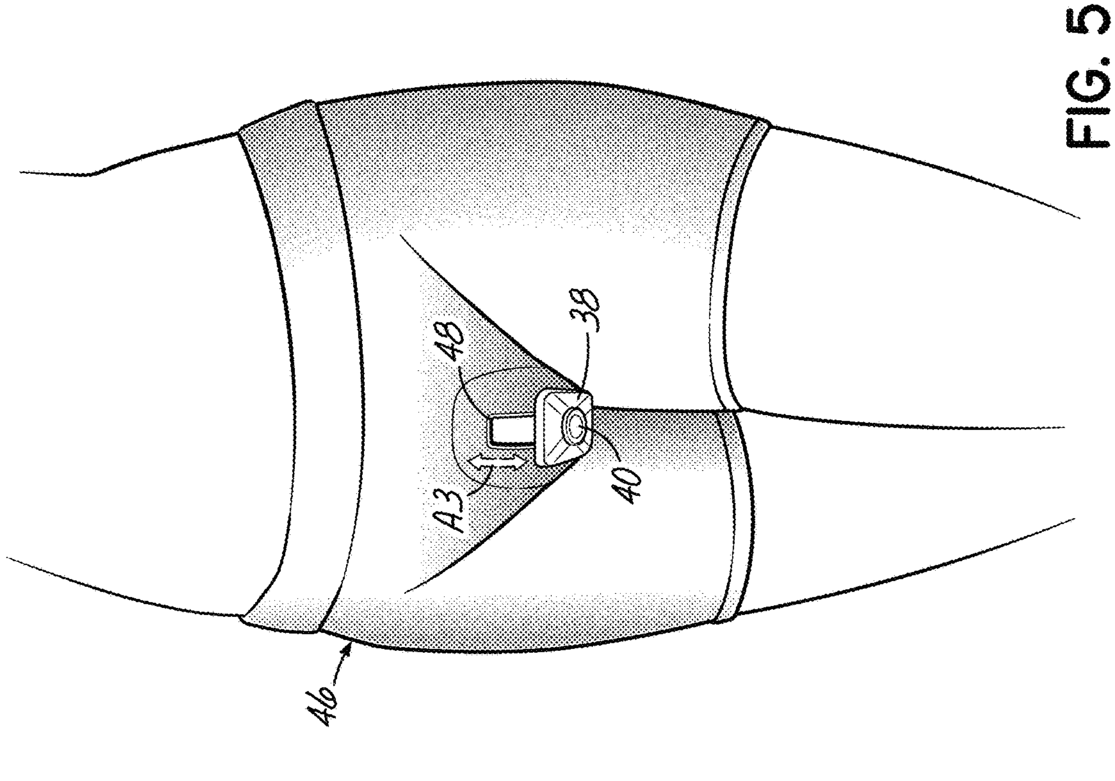
FIG. 5 is a perspective view of the micturition device and garment.

FIG. 5 shows the micturition device 12 engaged with a garment 46. Specifically, the Figure shows the fitting 38 of the slide plate 36 interacting with the slide track 48 of the garment 46. The garment could be a compression short, as shown in FIG. 5. Alternatively, the garment 46 could be a different undergarment. The garment 46 may be laundered between uses. In this embodiment, the "compression" nature of the compression short (e.g., garment 46) helps to ensure that the micturition cup 14 fits snugly against a wearer's anatomy. The track 48 is formed to engage with the cup, plate, and fitting 38. The track 48 could be formed of plastic and then glued, welded, or otherwise fixed to the garment 46. Alternatively, the track 48 could be formed of fabric such as by doubling and oversewing, or a similar technique, to create edges of the garment 46 for forming the track. If the track 48 is formed from a rigid material the fitting 38 could snap into engagement with the track 48.

Further, as illustrated by arrow A3, the fitting 38 is adjustable (e.g., slides) with respect to the track 48. Sliding the fitting 38 along the track 48 allows a user (wearer) to move the micturition device 12-particularly, the micturition cup 14. The position of the cup 14 can be adjusted along the length of track 48 for user comfort as well as to ensure that the cup 14 is properly placed in the vaginal area to capture fluids (e.g., urine, menstrual flow). Further, adjusting the position of the cup 14 ensures that the device 12 is more compatible with a user's body, the particular position of the user's body within a seat, for example, and helps to minimize pulling or strain on the disposable tube 18, for example.

Figure 6A:
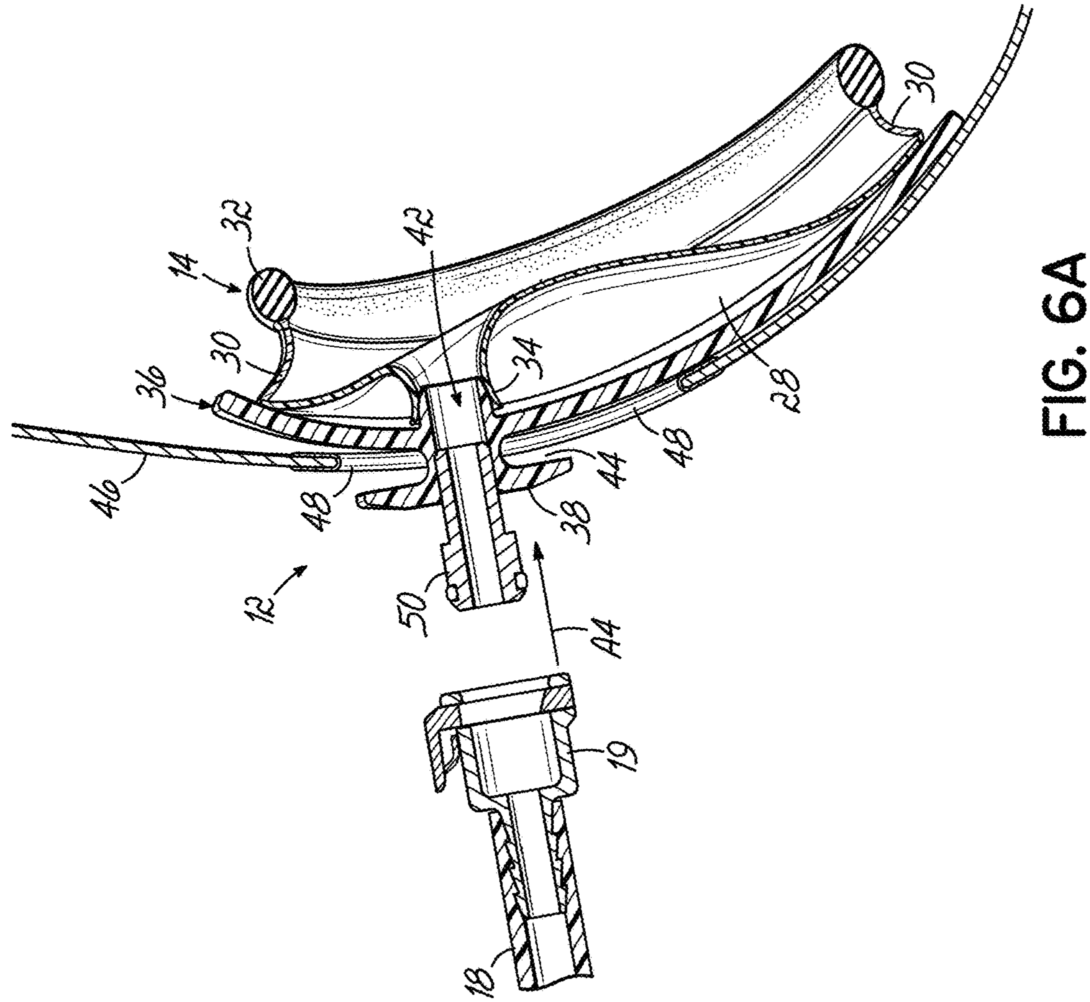
FIG. 6A is a cross-sectional view of the micturition device, connector, and garment.
Figure 6C:
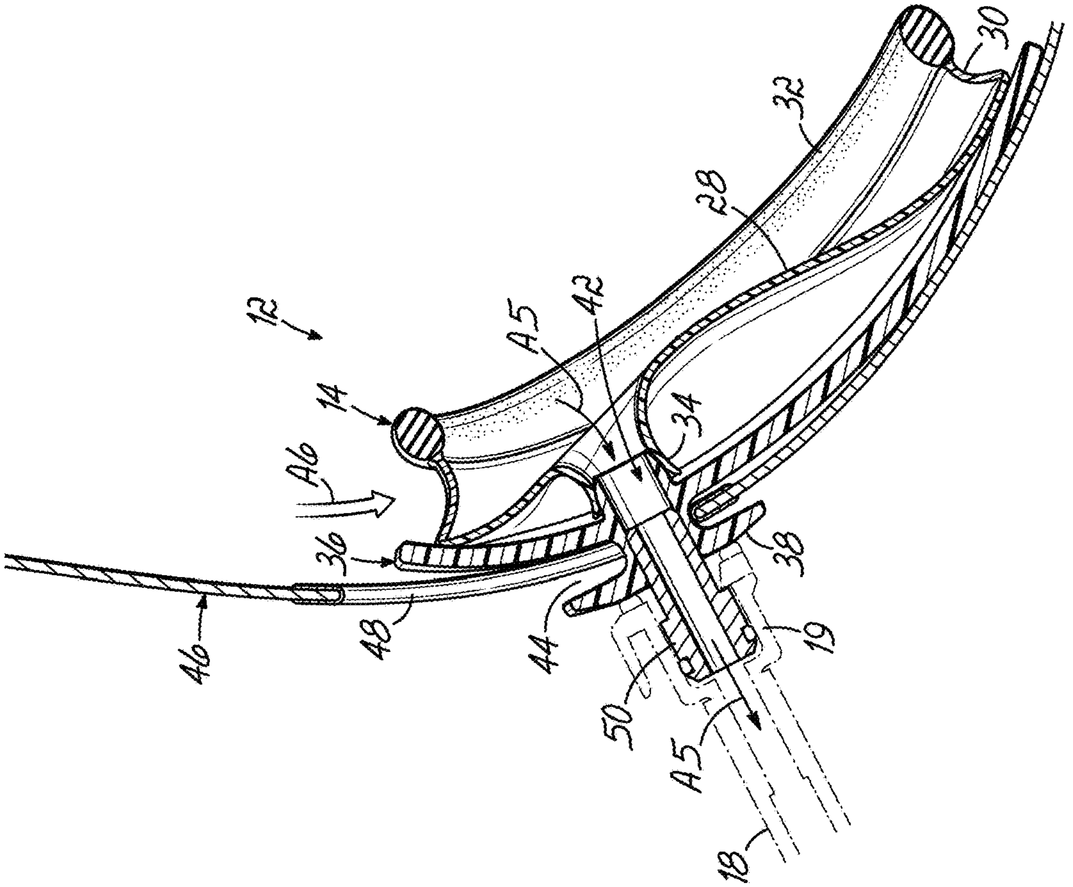
FIG. 6C is a further alternative cross-sectional view of the micturition device, connector, and garment.
Figure 6B:
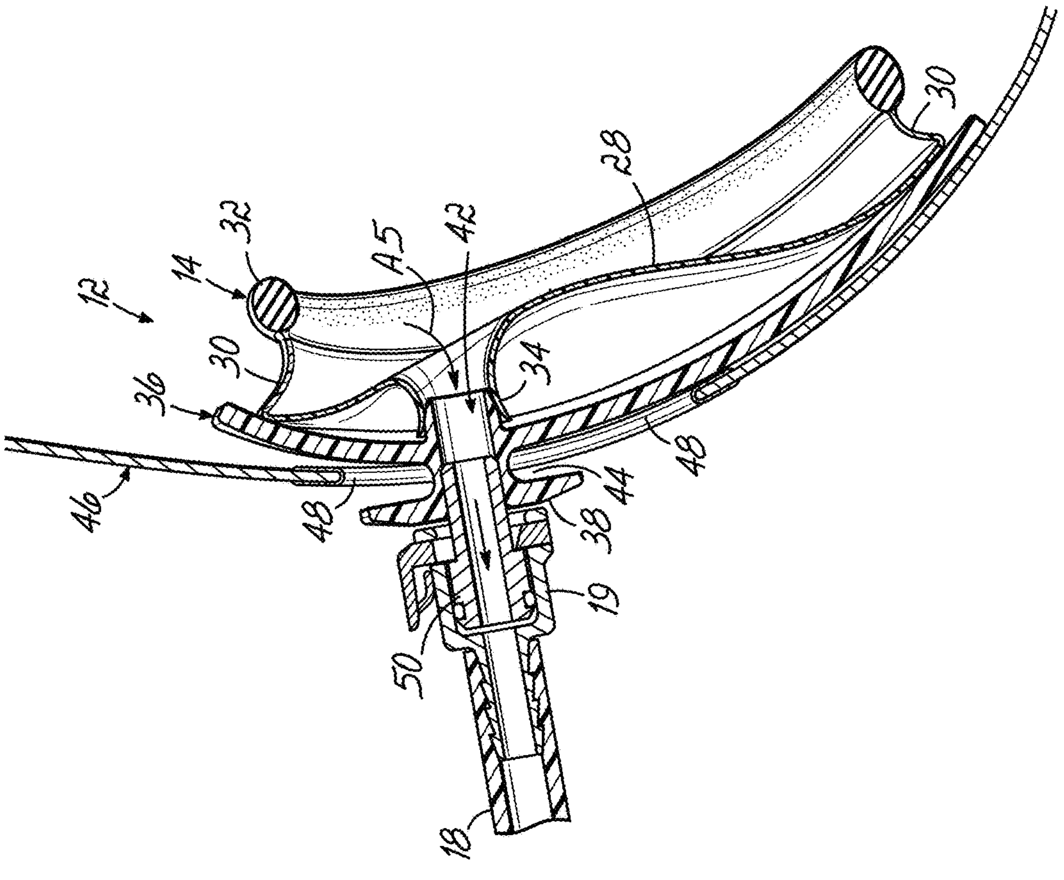
FIG. 6B is an alternative cross-sectional view of the micturition device, connector, and garment.

FIGS. 6A-6C show a cross-section of the micturition device 12 engaged with the sliding track 48 of the garment 46. Arrow A4 in FIG. 6A shows a connector 19, attached to a disposable tube 18, engaging with a connector adapter 50, attached to the fitting 38. A disposable tube 18 connects to the fitting 38 to dispose of the fluid through the micturition system 10. The connector 19 is a quick connect connector 19 that can quickly be attached and detached (e.g., snap fit) from the fitting 38-particularly, from the connector adapter 50 attached to the fitting 38. The connector 19 may also provide an audible "snap" sound when attached to the connector adapter 50. The "snap" provides audible feedback (e.g., to a wearer) that the disposable tube 18 is connected to the micturition device 12. Other connectors 19 (with or without a connector adapter 50) are contemplated. For example, the connector 19 could be threaded and screw into the fitting 38 or a connector adapter 50 engaged with the fitting. As such, the invention is not limited as to how the tube couples with fitting 38.

FIG. 6B shows the connector 19 attached to the connector adapter 50. Further, as illustrated by arrows A5, FIG. 6B (and FIG. 6C) shows the common flow path between the micturition cup 14 and the slide plate 36 formed by joining the outlet port 34 (of the cup 14) to the fitting 38 (of the slide plate 36). A fluid (e.g., urine, menstrual flow) flows from the outlet port 34, through the passage 42, through the connector adapter 50, through the connector 19, and into the disposable tube 18. From the disposable tube 18, the fluid is transported to the receptacle 16 by the rest of the micturition system 10. An interior of the disposable tube 18 or tube 20 may be coated with a coating material. The coating material may be hydrophobic to prevent fluid (e.g., urine) from sticking to the interior of the disposable tube 18 or tube 20 and to further encourage fluid to flow through the disposable tube 18 and tube 20. Alternatively, the coating material could be an anti-coagulant material to prevent a fluid (e.g., menstrual flow) from sticking to or accumulating within the disposable tube 18. For example, heparin might be used. Alternative coatings are also contemplated.

FIG. 6C shows that portions of the track 48 fit within the channels 44 of the fitting 38. This fit slidably secures the slide plate 36 to the garment 46 such that the micturition device 12 can be adjusted up and down within the bounds of the track 48, as illustrated by arrow A6.

For coupling the cup and fitting 30 to garment 46, the track 48 may be spread apart, due to the flexibility of the fabric, to allow the fitting to pass through or over the track and then engage the track with the cup on opposite sides as shown in FIG. 6A. The fitting 38 and plate 36 capture track 48 therebetween to allow for adjustability as disclosed. The edges of the slide track engage with the channels 44 formed around fitting to limit the side-to-side and top and bottom positions of the cup. Depending upon the construction of the track, such as more rigid plastic or softer fabric construction, the containment of the fitting and plate/cup may be more robust or softer and more forgiving. In an alternative embodiment, such as one using a relatively rigid plastic track, the track may not spread apart readily. In that scenario, it may ne necessary to make fitting 38 removable.

FIG. 7 shows an alternative embodiment of the micturition device 12. In this embodiment of the device 12, the micturition cup 14 and the slide plate 36 are integrally formed with each other. This embodiment does not require a separate slide plate 36. Rather, in this embodiment, the fitting 38 is separated or removable from the slide plate 36 or from the micturition device 12. Arrow A7 illustrates that the fitting 38 engages with the outlet port 34 of the device 12 to form a common flow passage. Therefore, to engage the track 38, the device 12 is positioned on an inside of the track, while the fitting 38 is positioned on an outside. The fitting 38 then may be aligned with port 34 and inserted to capture the track and complete the passage to a tube. Other than the alternative construction, the device 12 depicted in FIG. 7 functions like the device 12 as described above with respect to previous Figures (e.g., FIGS. 2A-4B).

Figure 8:
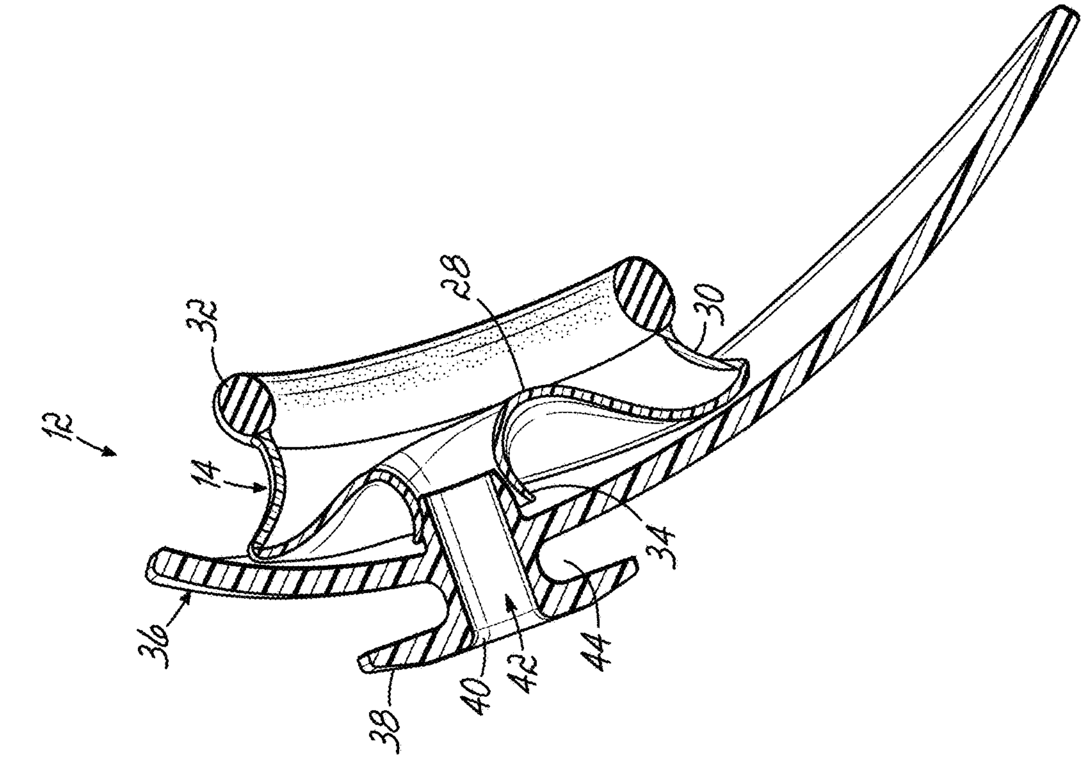
FIG. 8 is a cross-sectional view of a different alternative embodiment of the micturition device.

FIG. 8 shows a different alternative embodiment of the micturition device 12. In this embodiment of the device 12, the micturition cup 14 is smaller in dimension such that the cup 14 generally covers the urethral opening, but not the vaginal opening. This embodiment of the cup 14 is capable of collecting urine, but not capable of collecting other fluids such as menstrual flow. The length, width, and height of the cup 14 may vary depending on the intended use of the cup 14 (e.g., covering the urethra opening, but not the vaginal opening).

While the present invention has been illustrated by the description of various embodiments thereof, and while the embodiments have been described in considerable detail, it is not intended to restrict or in any way limit the scope of the appended claims to such detail. The various features discussed herein may be used alone or in any combination. For example, though the system 10 is described above for use by a female pilot, the system 10 could be adapted to the male anatomy to provide a less-invasive replacement for a catheter. Additionally, the described system 10 could be used in an environment other than a cockpit-in a hospital or home use, for example. Additional advantages and modifications will readily appear to those skilled in the art. The invention in its broader aspects is therefore not limited to the specific details and illustrative examples shown and described. Accordingly, departures may be made from such details without departing from the scope of the general inventive concept.

What is claimed is:

1. A micturition device for fluid removal, the micturition device comprising:

a garment configured to be worn over the pelvic area;

a micturition cup, the micturition cup being a unitary element configured to encircle vaginal area anatomy of a wearer including the urethral opening and vaginal opening of a wearer for capturing one or more fluids of the vaginal area anatomy, and being free of an element engaging a vaginal opening of the vagina;

the micturition cup including a semi-rigid cup floor of unitary construction and an outlet port in the cup floor for evacuating fluids from the micturition cup;

a unitary flexible sidewall that is a separate material from the cup floor and extends outwardly from an outside edge of the semi-rigid cup floor of the unitary micturition cup, the flexible sidewall material being more flexible than the semi-rigid cup floor material, the cup floor being contoured from the sidewall to the outlet port to direct the fluids to leave the cup;

a unitary rim gasket formed of a different material than the cup floor and sidewall, the rim gasket positioned atop a rim of the flexible sidewall and configured to surround the micturition cup, the rim gasket having a thickness greater than the flexible sidewall for molding and sealing around the vaginal area anatomy;

a slide plate having a complementary shape with the micturition cup, the slide plate including a semi-rigid slide fitting having a passage extending through the slide plate, the semi-rigid slide fitting having an end on a side thereof opposite the micturition cup that is spaced from the slide plate and forms a pair of semi-rigid channels, the slide fitting configured to connect, at an opposite end, to the outlet port of the micturition cup to join the micturition cup and the slide plate and to form a common flow passage from the micturition cup through the slide plate;

the garment including a rigid slide track, the micturition cup and slide plate being positioned in the garment on one side of the rigid slide track;

the slide fitting being positioned on the other side of the rigid slide track such that the slide track engages the pair of rigid channels between the slide plate and the slide fitting, the rigid channels engaging with the slide track so that the slide plate and micturition cup together slidably engage with and move along the slide track of the garment to adjust a position of the micturition device on the garment relative to the vaginal anatomy or a wearer.

2. The micturition device of claim 1, wherein the garment is a compression short, the compression short configured to hold the micturition cup securely in place.

3. The micturition device of claim 1, wherein the rigid slide track is made of plastic.

4. The micturition device of claim 1, wherein the rim gasket is formed from an elastomeric material.

5. The micturition device of claim 1, wherein the passage at the slide fitting end includes an orifice, the orifice configured to connect to a disposable tube to join the micturition cup to the disposable tube through the slide plate and to form the common flow passage from the micturition cup to the disposable tube for further evacuation of fluid from the micturition cup.

6. The micturition device of claim 1, wherein the micturition cup and the slide plate are integrally formed with each other.

7. The micturition device of claim 6, wherein the slide fitting is separate from the slide plate and micturition cup.

8. A method of using a micturition device, the method comprising:

providing a garment configured to be worn over the pelvic area of a wearer;

providing a micturition device for placement in the garment, the micturition device comprising:

a micturition cup, the micturition cup being a unitary element and configured to encircle vaginal area anatomy of the wearer of the garment including the urethral opening and vaginal opening of a wearer for capturing one or more fluids of the vaginal area anatomy, and being free of an element engaging a vaginal opening of the vagina:

the micturition cup including a semi-rigid cup floor of unitary construction and an outlet port in the cup floor for evacuating fluids from the micturition cup;

a unitary flexible sidewall that is a separate material from the cup floor and extends outwardly from an outside edge of the semi-rigid cup floor of the unitary micturition cup, the flexible sidewall material being more flexible than the semi-rigid cup floor material, the cup floor being contoured from the sidewall to the outlet port to direct the fluids to leave the cup;

a unitary rim gasket formed of a different material than the cup floor and sidewall, the rim gasket positioned atop a rim of the flexible sidewall and configured to surround the micturition cup, the rim gasket having a thickness greater than the flexible sidewall for molding and sealing around the vaginal area anatomy;

a slide plate having a complementary shape with the micturition cup, the slide plate including a semi-rigid slide fitting having a passage extending through the slide plate, the rigid slide fitting having an end on a side thereof opposite the micturition cup that is spaced from the slide plate and forms a pair of semi-rigid channels, the slide fitting configured to connect, at an opposite end, to the outlet port of the micturition cup to form a common flow passage from the micturition cup through the slide plate; and the garment including a rigid slide track, the micturition cup and slide plate being positioned in the garment against the wearer on one side of the rigid slide track;

the slide fitting being positioned on the other side of the rigid slide track such that the slide track engages the pair of rigid channels between the slide plate and the slide fitting, the rigid channels engaging with the slide track;

attaching the slide plate to the garment by engaging the slide fitting with the slide track so that the slide plate and micturition cup together slidably engage with and move along the slide track;

moving the slide plate along the slide track of the garment to adjust a position of the micturition device on the garment relative to the vaginal anatomy or a wearer.

9. The method of claim 8, the method further comprising attaching a disposable tube to the fitting to form the common flow passage from the micturition cup to the disposable tube for further evacuation of fluid from the micturition cup.

10. The method of claim 9, the disposable tube comprising a connector to interface with the slide fitting of the slide plate.

11. A micturition system for fluid removal, the micturition system comprising:

a garment configured to be worn over the pelvic area;

a micturition device, the micturition device comprising:

a micturition cup, the micturition cup being a unitary element and configured to encircle vaginal area anatomy of the wearer of the garment including the urethral opening and vaginal opening of a wearer for capturing one or more fluids of the vaginal area anatomy, and being free of an element engaging a vaginal opening of the vagina;

the micturition cup including a semi-rigid cup floor of unitary construction and an outlet port in the cup floor for evacuating fluids from the micturition cup;

a unitary flexible sidewall that is a separate material from the cup floor and extends outwardly from an outside edge of the semi-rigid cup floor of the unitary micturition cup, the flexible sidewall material being more flexible than the semi-rigid cup floor material, the cup floor being contoured from the sidewall to the outlet port to direct the fluids to leave the cup;

a unitary rim gasket formed of a different material than the cup floor and sidewall, the rim gasket positioned atop a rim of the flexible sidewall and configured to surround the micturition cup, the rim gasket having a thickness greater than the flexible sidewall for molding and sealing around the vaginal area anatomy;

a slide plate having a complementary shape with the micturition cup, the slide plate including a semi-rigid slide fitting having a passage extending through the slide plate, the semi-rigid slide fitting having an end on a side thereof opposite the micturition cup that is spaced from the slide plate and forms a pair of semi-rigid channels, the slide fitting configured to connect, at an opposite end, to the outlet port of the micturition cup to join the micturition cup and the slide plate and to form a common flow passage from the micturition cup through the slide plate; and the garment including a rigid slide track, the micturition cup and slide plate being positioned in the garment on one side of the slide track to slidably engage with the rigid slide track;

the slide fitting being positioned on the other side of the rigid slide track such that the slide track engages the pair of rigid channels between the slide plate and the slide fitting, the rigid channels engaging with the slide track so that the slide plate and micturition cup together slidably engage with and move along the slide track of the garment to adjust a position of the micturition device on the garment relative to the vaginal anatomy or a wearer;

a disposable tube, the disposable tube configured to connect to the slide fitting to transport fluid away from the micturition cup;

a vacuum tube, the vacuum tube configured to connect to the disposable tube to transport fluid away from the disposable tube;

a receptacle, the receptacle configured to connect to the vacuum tube and to receive fluid from the vacuum tube;

a vacuum source, the vacuum source configured to connect to the vacuum tube and to create a negative pressure to draw a fluid away from the micturition cup; and a pressure controller, the pressure controller configured to adjust the negative pressure.

12. The micturition system of claim 11, wherein the micturition system further includes a bag configured to transport and store the receptacle and vacuum source.

13. The micturition system of claim 11, wherein the pressure controller has at least a low pressure setting and a high pressure setting.

* * * * *